US008893109B2

(12) United States Patent
Birtwhistle et al.

(10) Patent No.: US 8,893,109 B2
(45) Date of Patent: Nov. 18, 2014

(54) SOFTWARE DISTRIBUTION AMONGST MEDICAL DEVICES TAKING INTO ACCOUNT DEPENDENCIES BETWEEN DEVICES

(75) Inventors: Daniel P. Birtwhistle, Fishers, IN (US);
Igor Gejdos, Indianapolis, IN (US);
Robert E. Reinke, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 459 days.

(21) Appl. No.: 13/195,917

(22) Filed: Aug. 2, 2011

(65) Prior Publication Data
US 2013/0036412 A1   Feb. 7, 2013

(51) Int. Cl.
*G06F 9/44* (2006.01)
*G06F 9/445* (2006.01)
*G06F 19/00* (2011.01)

(52) U.S. Cl.
CPC .............. *G06F 19/3412* (2013.01); *G06F 8/61* (2013.01); *G06F 8/67* (2013.01); *G06F 8/65* (2013.01); *G06F 8/60* (2013.01)
USPC ............ 717/171; 717/168; 717/170; 717/177

(58) Field of Classification Search
CPC .............. G06F 8/65; G06F 8/67; G06F 8/60; G06F 8/61; G06F 19/3412; H04L 29/06
See application file for complete search history.

(56) References Cited

U.S. PATENT DOCUMENTS

| | | | |
|---|---|---|---|
| 6,202,207 B1 | 3/2001 | Donohue | |
| 7,904,608 B2 | 3/2011 | Price | |
| 7,987,449 B1* | 7/2011 | Marolia et al. | 717/120 |
| 2002/0144254 A1* | 10/2002 | Owada | 717/171 |
| 2003/0009753 A1* | 1/2003 | Brodersen et al. | 717/172 |
| 2003/0221190 A1* | 11/2003 | Deshpande et al. | 717/171 |
| 2006/0184927 A1* | 8/2006 | Deblaquiere et al. | 717/168 |
| 2007/0074197 A1* | 3/2007 | Buckley et al. | 717/168 |

(Continued)

FOREIGN PATENT DOCUMENTS

EP   1722310   11/2006

OTHER PUBLICATIONS

Andre van der Hoek, Software release management for component-based software, 2003, pp. 77-95.*

(Continued)

*Primary Examiner* — Thuy Dao
*Assistant Examiner* — Mongbao Nguyen
(74) *Attorney, Agent, or Firm* — Harness, Dickey & Pierce, P.L.C.

(57) ABSTRACT

A computer-implemented method is provided for distributing product updates from a configuration device to one or more handheld medical device. The method includes: receiving a request to download a product update to a requesting medical device; determining dependencies that must be met before the product update can be downloaded to the requesting medical device, where at least one of the dependencies specifies a version of software that resides on a device which is interoperable with the requesting medical device; receiving a listing of peer devices from the requesting medical device; determining software residing on a given peer device for each peer device in the listing of peer devices; comparing the at least one dependency with the software residing on each peer device in the listing of peer devices; and distributing the product update to the requesting medical device when the at least one dependency is met.

16 Claims, 10 Drawing Sheets

(56) References Cited

U.S. PATENT DOCUMENTS

| | | |
|---|---|---|
| 2007/0169103 A1* | 7/2007 | Bhatkhande et al. ......... 717/170 |
| 2007/0240147 A1* | 10/2007 | Bernabeu-Auban et al. . 717/170 |
| 2007/0240152 A1 | 10/2007 | Li et al. |
| 2008/0028395 A1* | 1/2008 | Motta et al. ................... 717/177 |
| 2008/0134164 A1* | 6/2008 | Stich et al. .................... 717/172 |
| 2008/0300919 A1 | 12/2008 | Charlton et al. |
| 2008/0301665 A1 | 12/2008 | Charlton et al. |
| 2009/0106748 A1* | 4/2009 | Chess et al. ................... 717/168 |
| 2009/0133014 A1* | 5/2009 | Laurila et al. ................. 717/174 |
| 2009/0265701 A1* | 10/2009 | Naslavsky et al. ............. 717/172 |
| 2010/0125839 A1 | 5/2010 | Gebis et al. |
| 2010/0251232 A1* | 9/2010 | Shinomiya .................... 717/177 |
| 2010/0287543 A1* | 11/2010 | Wehkamp ..................... 717/171 |
| 2011/0035739 A1* | 2/2011 | Harada ......................... 717/168 |
| 2011/0173599 A1* | 7/2011 | Ohama et al. ................. 717/168 |
| 2011/0321030 A1* | 12/2011 | Rajan et al. ................... 717/170 |
| 2011/0321031 A1* | 12/2011 | Dournov et al. .............. 717/171 |

OTHER PUBLICATIONS

Jose L. Ruiz, A Framework for Resolution of Deloyment Dependencies in Java-Enabled Service Gateways, 2004, pp. 1-10.*

Herve Roussain, Cooperative Component-Based Software Deployment in Wireless Ad Hoc Networks, 2005, pp. 1-12.*

Code of Federal Regulations, Title 21, Chapter I "Food and Drug Administration Department of Health and Human Services Subchapter H—Medical Devices" Apr. 1, 2010.

Dexcom SEVEN® PLUS Software, www.dexcom.com/products/dm3_software, 3 pages.

* cited by examiner

SOFTWARE DISTRIBUTION AMONGST MEDICAL DEVICES TAKING INTO ACCOUNT DEPENDENCIES BETWEEN DEVICES

FIELD

The present disclosure relates generally to a digital distribution platform and, more particularly, to a method for distributing product updates to portable medical device that takes into account dependencies with other devices which are interoperable with the medical device.

BACKGROUND

Increasingly, the healthcare industry is turning to portable electronic medical devices to assist with care of patients. For example, a diabetes patient may use a blood glucose meter, an insulin pump, and/or a continuous glucose meter as part of the patient's medical treatment. Each of these devices is configured with suitable software for operating the device. Over time, the software and firmware and its associated data files may need to be updated. In the past, the patient was required to send the device back to the device manufacturer for updating. The device manufacturer would in turn install new versions of the software on the medical device and return the updated device back to the patient. In other situations, a device manufacturer may have sent a computer readable disk which contains updated versions of the software to either the patient or their healthcare provider, such that disk could used to update the software on the medical device. Each of these approaches has drawbacks.

Thus, there is a need for a digital distribution platform that can be used to publish and distribute product updates to portable medical devices. Rather than receive product updates directly from a device manufacturer, it may be more preferable for patients to receive product updates from an intermediary such as their health care provider. In this regard, the distribution platform should support distribution of product updates through an intermediary to the portable medical devices. Moreover, a given device may be interoperable with a plurality of other devices, and therefore any distribution method should take into account dependencies with other devices which are interoperable with the given device.

This section provides background information related to the present disclosure which is not necessarily prior art.

SUMMARY

In one aspect the present disclosure, a computer-implemented method is provided for distributing product updates from a configuration device to one or more handheld medical device(s). The method includes: receiving a request to download a product update to a requesting medical device; determining dependencies that must be met before the product update can be downloaded to the requesting medical device, where at least one of the dependencies specifies a version of software that resides on a device which is interoperable with the requesting medical device; receiving a listing of peer devices from the requesting medical device, such that each peer device in the listing of peer devices is distinct from and interoperable with the requesting medical device; determining software residing on a given peer device for each peer device in the listing of peer devices; comparing at least one dependency with the software residing on each peer device in the listing of peer devices; and distributing the product update to the requesting medical device when at least one dependency is met. In one implementation, the product update is distributed to the requesting medical device when the software residing on the each peer device has a version as recent as the version of software specified by the at least one dependency.

The method may further include receiving an identifier for the geographic region associated with the requesting medical device, comparing the identifier to another dependency; and distributing the product update to the requesting medical device when the another dependency is met, where the another dependency specifies an intended geographic area of use for the product update.

In one implementation, the software available for distribution by the configuration device may be downloaded to the configuration device over a telecommunication network from a distribution server and stored in a data store residing on the configuration device.

Likewise, a dependency file that contains dependencies for one or more product updates may be downloaded to the configuration device from the distribution server.

The listing of peer devices may be maintained by the given medical device and communicated to the configuration device from the requesting medical device. The listing may further include an enumeration of software residing on each peer device in the listing.

In another aspect of the disclosure, a software configuration device is provided for distributing product updates to one or more handheld medical devices. The configuration device includes: a distribution data store that stores one or more product updates available for distribution; a dependency file that store one or more dependencies for a given product update that must be met before the product update can be downloaded; and an update distributor configured to receive a request to download the product update from a requesting medical device and distribute the product update to the requesting medical device when applicable. In response to the download request, the update distributor retrieves one or more dependencies for the product update from the dependency file, where at least one of the dependencies for the product update specifies a version of software that resides on a device which is interoperable with the requesting medical device. The update distributor is further configured to receive a listing of peer devices that are interoperable with the requesting medical device and, in response to the download request, compare the at least one dependency with software residing on each peer device in the listing of peer devices and distribute the given product update to the requesting medical device when the at least one dependency is met.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

Figure 1:
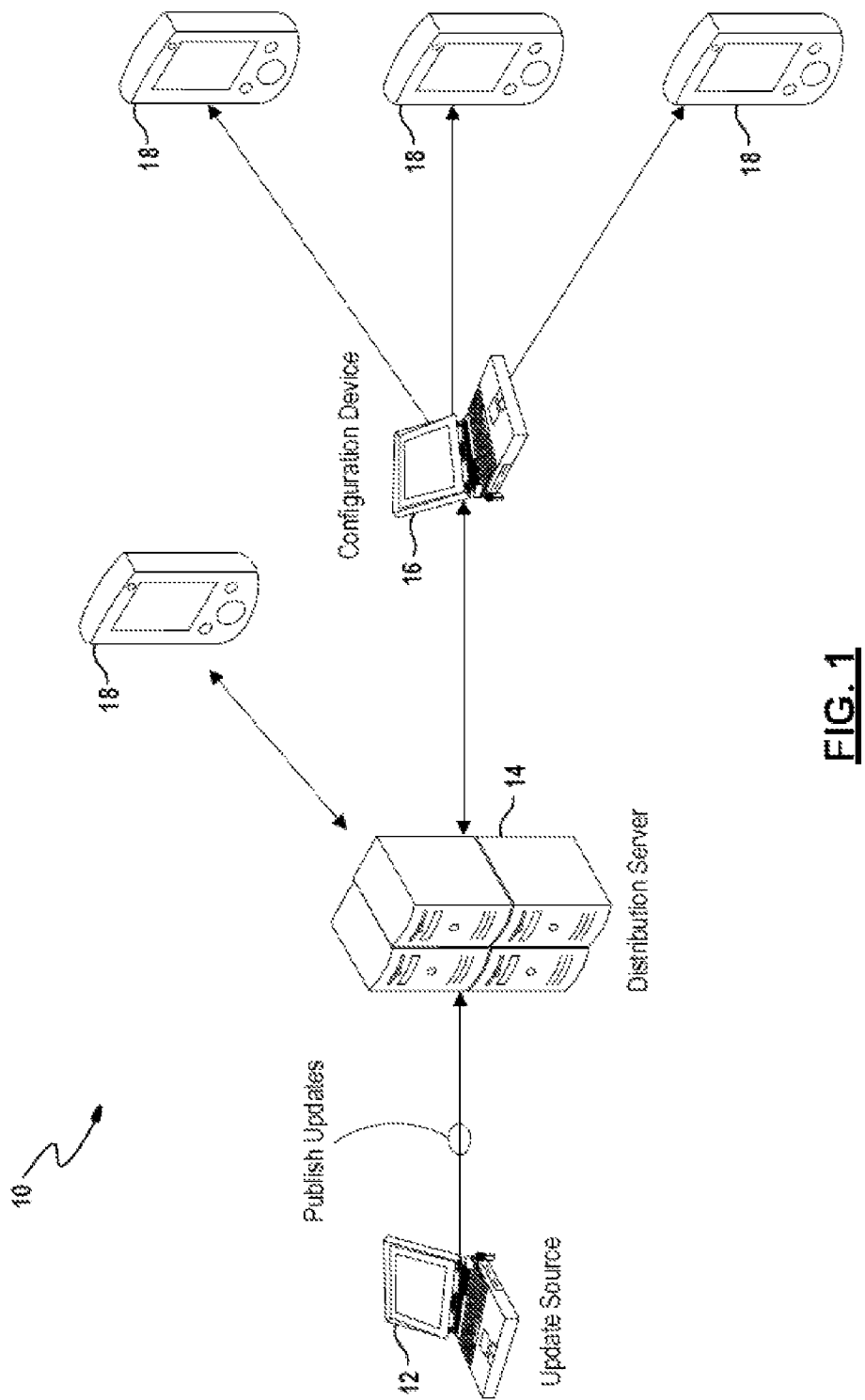
FIG. 1 is a diagram depicting an exemplary digital distribution platform for distributing product updates to end user medical devices.

The drawings described herein are for illustrative purposes only of selected embodiments and not all possible implementations, and are not intended to limits the scope of the present disclosure. Corresponding reference numerals indicate corresponding parts throughout the several views of the drawings.

DETAILED DESCRIPTION

FIG. 1 depicts an exemplary digital distribution platform 10 for distributing product updates to handheld medical devices such a blood glucose meter or an insulin pump. The distribution platform 10 is comprised generally of: an update source 12, a distribution server 14, a configuration device 16 and one or more medical devices 18. Each of the components is further described below. While the following description is provided with reference to medical devices, it is readily understood that the concepts disclosed herein are applicable more generally to other types of portable consumer electronic devices.

The update source 12 enables users to publish or otherwise make available product updates for medical devices 18 via the distribution server 14. Product updates are files that contain updates for a device. For example, a product update can be an update to a software application, firmware, a language file, and/or a database residing on the device. Product updates can also encompass updates to device parameters, user documentation or other types of data files. Other types of product updates are also contemplated by this disclosure. In an exemplary embodiment, the update source 12 is further defined as a desktop personal computer or some other computing device having access over a network to the distribution server 14.

Figure 2:
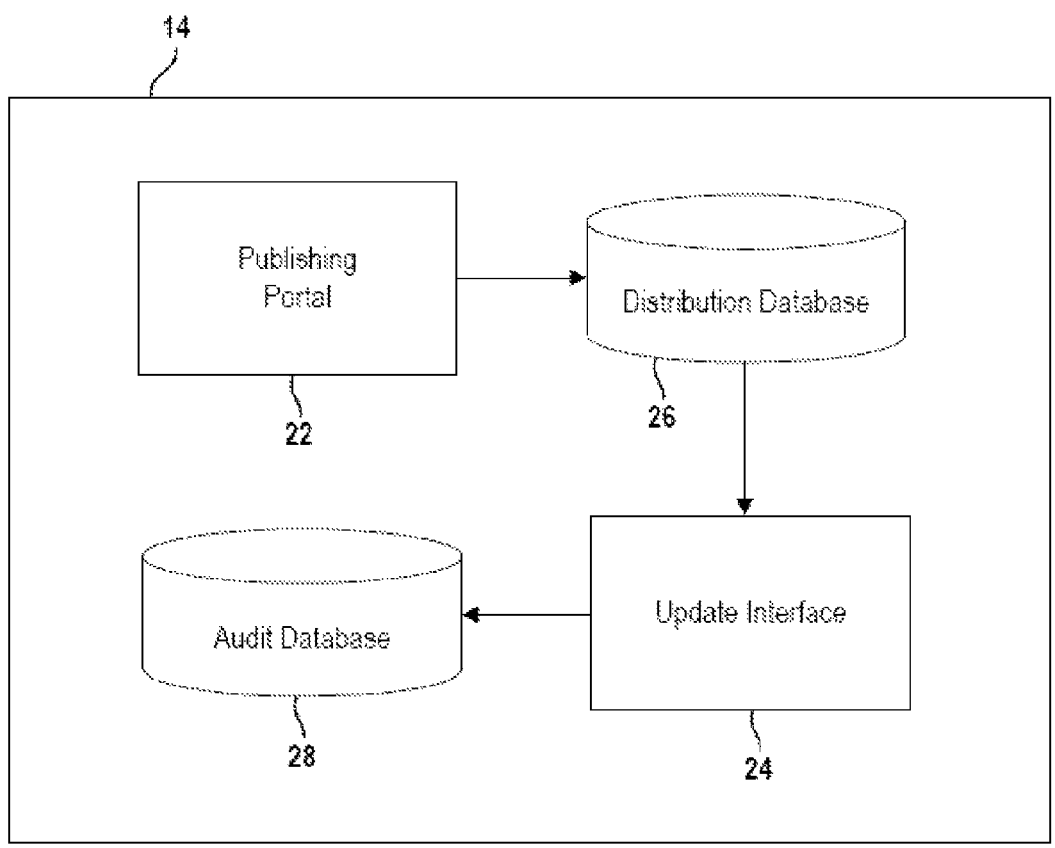
FIG. 2 is a diagram depicting an exemplary construct for the distribution server.

FIG. 2 further illustrates an exemplary construct for the distribution server 14. The distribution server 14 includes a publishing portal 22, an update interface 24, a distribution database 26 and an audit database 28. The publishing portal 22 provides an interface to publish product updates. In an exemplary embodiment, the portal 22 may be one or more web pages accessible by the update source 12. Publishers of product updates may use the portal 22 to configure the parameters associated with the product update. For example, the publisher may specify one or more countries for which the product update is to be available. In another example, the publisher may specify conditions or dependencies which must be meet to install the product update. The portal 22 then publishes the product update by creating an entry for the product update in the distribution database 26. Further details regarding an exemplary publishing portal 22 may be found in U.S. patent application Ser. No. 13/195,975 entitled "Remote Configuration and Selective Distribution of Product Content to Medical Device" filed concurrently herewith and incorporated herein by reference.

Figure 5:
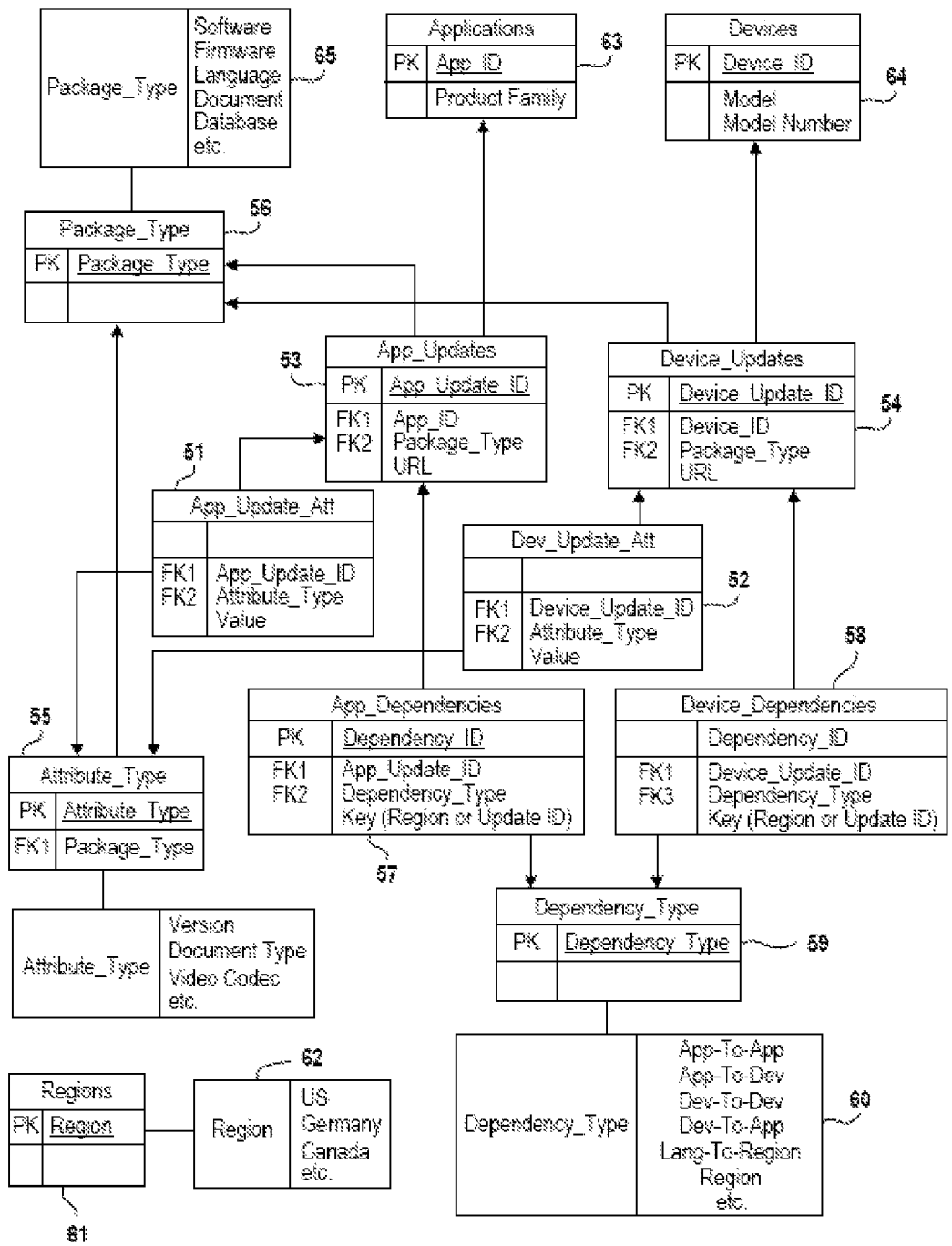
FIG. 5 is a diagram of an exemplary data model for the distribution database.

FIG. 5 depicts exemplary data model for how the distribution database 26 could be constructed. Of note, the data model supports defining dependencies between products (i.e., applications) as well as devices. Dependencies are used in order to determine if a product is capable of being updated as further described below.

More specifically, the data model includes an application update attribute element 51 and a device update attribute element 52. The application update attribute element 52 includes foreign keys relating the application update attribute element 52 to an application update element 53 and an attribute type element 55. Similarly, a device update attribute element 52 has foreign keys relating the update attribute element 52 to a device update element 54 and the attribute type element 55. The attribute type 55 stores an attribute type and include a foreign key that relates the attribute type 55 to a package type element 56. Examples of attribute types include a version, a document type or a video codec.

The data model further includes an application dependency element 57 and a device dependency element 58. The application dependency element 57 has a primary key indicating a dependency identifier for the application, and foreign keys that relate an application dependency element 57 to the application update element 53 and a dependency type element 59. Similarly, the device dependency element 58 includes a primary key indicating a dependency identifier, as well as foreign keys that relate a device dependency element 58 to a device update element 54 and a dependency type element 59. Both the application dependency element 57 and the device dependency element 58 can include a key that references a region element 61 or another update id.

The dependency type element 59 defines a type of dependency. Examples of dependency types include a device-to-device dependency, meaning that an update or action must be performed on one device in order for an update can be applied to another device. Another example of a dependency type is an application-to-application, meaning that an update or action must be performed on one application in order for a requested update to be applied to another application. The dependency types can also include device-to-application, language-to-region, regional dependencies, and other update dependencies.

The application update attribute element 51 and the application dependency element 54 both relate to the application update element 53. Similarly, the device update attribute element 52 and the device dependency element 58 both point to the device update element 54. The application update element 53 includes a primary key of an application update identifier and foreign keys that relate an application update element 53 to an application element 63 and to a package type element 56. The application update element 53 can also store a location of an application update file corresponding to the update package, e.g. the URL of the application update file. The device update element 54 includes a primary key indicating a device update identifier and foreign keys that relate a device update element 54 to a device element and the package type element. The device update element 54 can also store a location of a device update file corresponding to the update package.

Application update elements 53 relate to an application element 63 and device update elements 54 relate to a device element 64. The application element 63 includes a primary key indicating an application identifier. The application element 63 can further store the product family members of the application, including the products that the application can execute on. The device element 64 includes a primary key that indicates a device identifier and can further store a model and model number of the device.

The package type element 56 is referenced by the application update element 53, the device update element 54 and the attribute type element 55. The package type element 56 includes a package type as a primary key. Examples of package types include a software update, a firmware update, a language update, a document update, and a database update. The region element 61 may be referenced by a dependency element 57 or 58. The region element can include a list of regions that an update is intended for. The regions can be countries, continents, geographical regions, or another geographical division. It is appreciated that the foregoing is an exemplary structure of the distribution database 26. It is appreciated that variations of the foregoing are contemplated and within the scope of this disclosure.

With continued reference to FIG. 2, the update interface 24 is configured to distribute product updates published in the distribution database 26. When a requesting device queries the update interface 24 for the latest versions of available product updates, the update interface 24 responds by querying the distribution database 26 and provides a listing of available product updates to the requesting device. The update interface 24 may subsequently receive a request to download a particular product update. In response to the download request, the update interface 24 will download the product update to the requesting device and maintain a record of the download in the audit database 28. Each of these functions is further described below.

Figure 3:
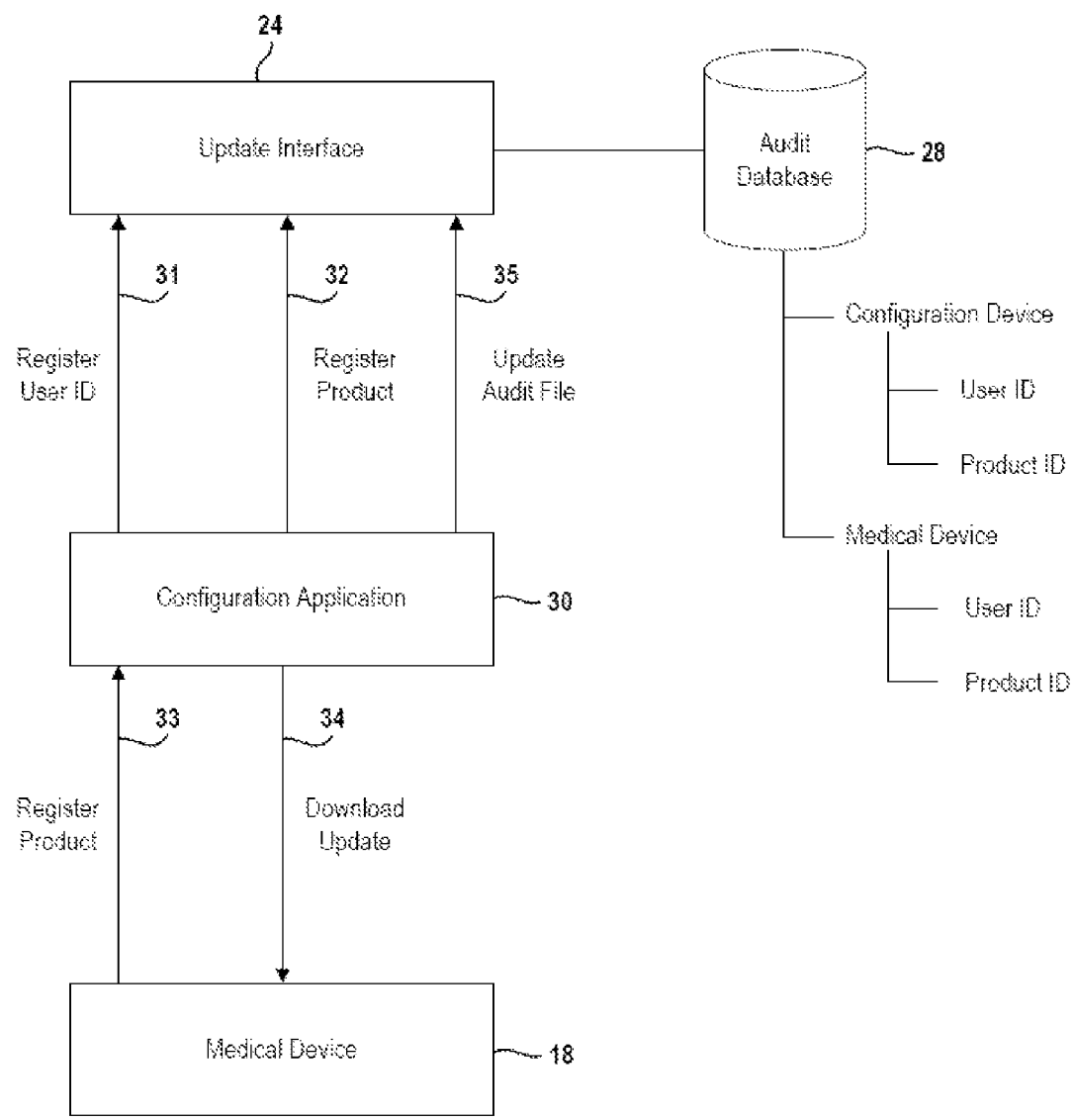
FIG. 3 is a diagram depicting an exemplary method for distributing product updates through an intermediary using the digital distribution platform.

FIG. 3 illustrates an exemplary method for distributing product updates through an intermediary using the digital distribution platform 10. In an exemplary use case, product updates may be downloaded from the distribution server 14 to an intermediary, such as a health care provider. More specifically, the product updates are downloaded to a configuration application 30 residing on a configuration device 16 associated with the health care provider. In an exemplary embodiment, the configuration device 16 is a desktop personal computer residing at the office of the health care provider. The healthcare provider will in turn download product updates to the medical devices of their patients. To do so, patients will typically bring their medical devices with them when visiting their healthcare provider. The medical devices 18 can communicate either via a wired or wireless connection with the configuration device 16. For regulatory compliance, it is important to capture information regarding the identity of the healthcare provider distributing product updates as well as the identity of the medical device receiving product updates.

Upon installation of a configuration application 30 on a configuration device 16 or sometime thereafter, the configuration application 30 will operate to register itself with the update interface 24 provided by the distribution server 14. Registration will include capturing information at 31 that uniquely identifies the healthcare providing entity associated with the configuration application, where a healthcare providing entity is understood to be an individual, such as physician or a nurse, or a collection of individuals such as group medical practice or a hospital. Exemplary identifying information for a healthcare provider may include name, address, practitioner license number, and the like. Registration will also include capturing information at 32 that uniquely identifies the configuration application (i.e., ApplicationInfo) and/or the configuration device. Exemplary identifying information for a unique application may include the product family, an application identifier, a version number for the application currently installed as well as other types of identifying information. Such identifying information may be gathered by querying a user or some other suitable method. Captured registration information will then be communicated to and stored by the update interface 24. Once properly registered, the configuration application 24 can interface with the update interface 24 to retrieve product updates from the distribution server 14.

Figure 4:
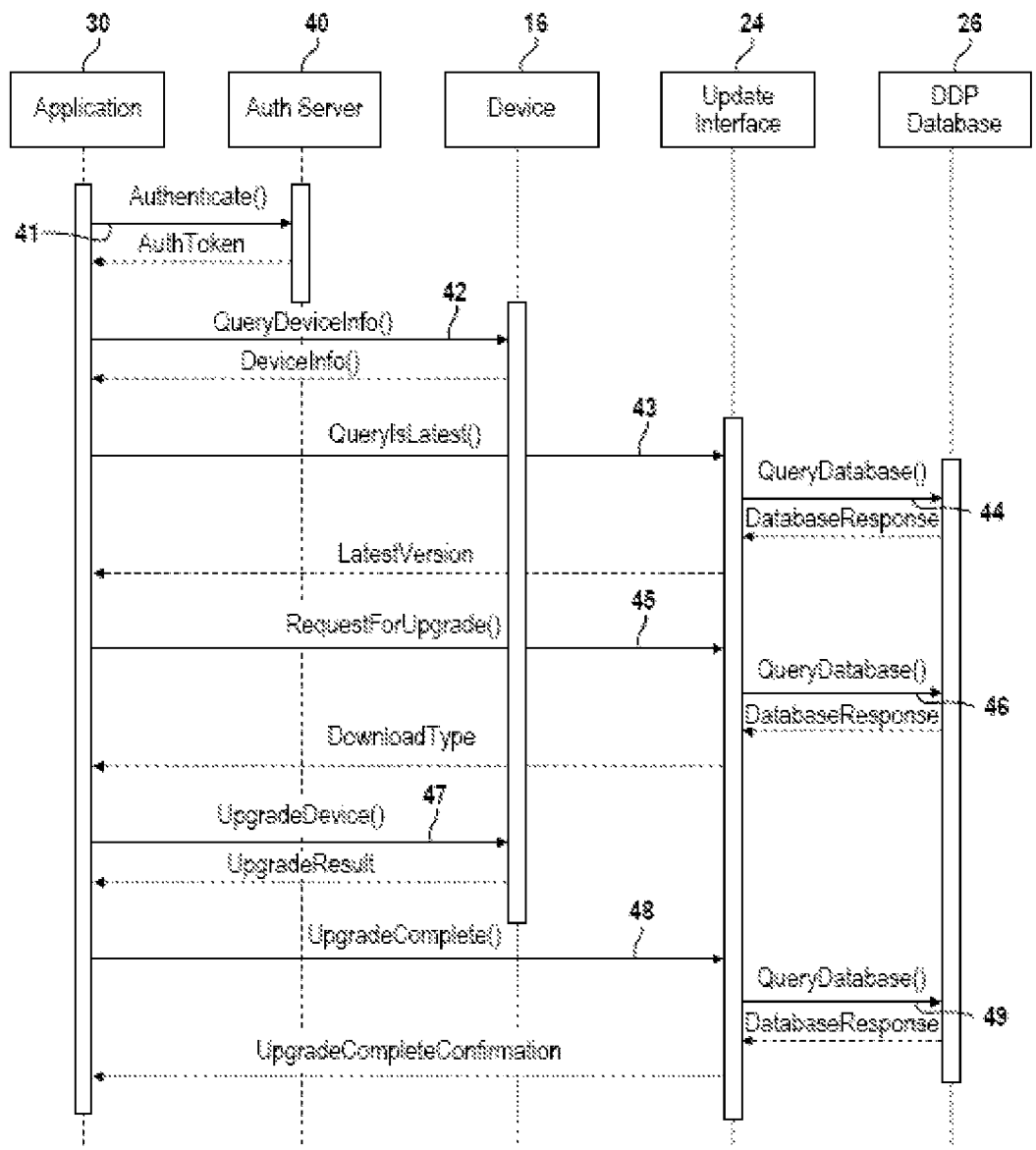
FIG. 4 is a diagram depicting an exemplary method by which a configuration application retrieves product updates from the distribution server.

In an exemplary embodiment, the configuration application 30 operates to retrieve product updates from distribution server 14 as shown in FIG. 4. Before querying the update interface for available updates, the configuration application may first authenticate at 41 with an authenticating entity 40. The authentication entity may reside on a separate distinct server or the distribution server. When successfully authenticated, the authentication entity 40 returns an authentication token to the configuration application 30. Various authentication schemes are readily known and are suitable for use in this context. The configuration application 30 may then use the authentication token while interfacing with the distribution server 14.

The configuration application 30 may optionally query the device it resides on at 42 to learn identifying information for the device (i.e., DeviceInfo). Exemplary identifying information may include a model of the device, a current model number for the device, a device type, a serial number for the device, a version number for firmware currently installed on the device as well as other identifying information. The identifying information is returned to the configuration application 30 in response to the query. In other embodiments, identifying information for the device may be determined at installation and retained for subsequent use by the configuration application 30.

To initiate a download, the configuration application 30 first queries the update interface at 43 for available product updates. The query will include identifying information for either the configuration application or the configuration device. The query may include information that further identifies the request such as the region or geographic location of the product. The query may also include an authentication token for authenticating the request at the distribution server. This information may be used to constrain the query results. For example, a given configuration application may support only certain products and thus only a listing of updates for the supported products are provided in the query results. Similarly, geographic location may be used to provide a listing of available product updates applicable to the geographic location. Since medical devices are typically regulated at a country level, distribution of product updates should be controlled on a country basis or within some other applicable geographic area, such as countries forming the European Union.

Upon receipt of the query, the update interface 24 would in turn query the distribution database 26 at 44 to determine product updates available to the configuration device and communicate a listing of available product updates back to the configuration device in response to the query.

Given a list of available product updates, the configuration application 30 is configured to retrieve one or more product updates from the distribution server 14. For example, the configuration application 30 may scroll through the listing of available product updates. In an exemplary embodiment, product updates are segmented as packages. Thus, each entry in the listing will include a package identifier, a package type (e.g., software, firmware, language, document, database, etc.), and a version number for the package. Each update may further include a version and any dependencies associated with that update version. For each package, the configuration application 30 may compare the version of the package to a listing previously downloaded packages. When a more current version of a package is available, the configuration application 30 will make a request for an upgrade as indicated at 45.

Upon receipt of a download request from the configuration application 30, the update interface 24 will query at 46 the distribution database 26. In one exemplary embodiment, the update interface 24 retrieves the data (or files) comprising the product update from the distribution database 26 and forwards the product update to the configuration device 16. In another embodiment, a uniform resource locator (URL) is retrieved and returned to the configuration application. The URL can then be used by the configuration application 30 to download the product update. The URL may be accompanied by a listing of the files in the requested package, their respective sizes and signatures. Other implementations for downloading updates by the configuration device fall within the broader aspects of this disclosure. In any case, the configuration application 30 upgrades the device at 47 with the downloaded updates. For updates pertaining to the configuration device, the upgrades may be immediately implemented by the configuration application. On the other hand, updates intended for medical devices 18 are stored in a data store on the configuration device 16 and thereby made available for subsequent download by such devices.

Once the upgrade has been completed, the configuration application 30 may verify the upgrade attempt. For example, the configuration application may compile a report enumerating the result of the upgrade attempt associated with the requested package. A message reporting the result of the upgrade is then communicated at 48 from the configuration application 30 to the update interface 24. The confirming message may be a singular status indicator (e.g., successful or failure) and/or include the more comprehensive report compiled by the configuration application. Lastly, the configuration application 30 will update at 49 the audit database 28 with an entry regarding the download to the configuration device 16. Thus the audit database 28 creates a log of the updates downloaded to the configuration application 30, including information identifying the user or owner of the configuration application and information identifying the configuration application or the device it resides on.

Likewise, for medical devices receiving product updates, it is important to capture information identifying these medical devices and/or the users thereof. With continued reference to FIG. 3, each medical device 18 will register itself at 33 with the configuration application 30 associated with the patient's healthcare provider. Such registration is required before a medical device can download updates from the configuration application. During registration, the configuration application 30 will capture information that uniquely identifies the medical device (e.g., device serial number). Although not required in all embodiments, the configuration application 30 may also capture information that uniquely identifies the healthcare recipient or user of the device. This type of information may be captured by querying the device for such information or querying the user directly. In most scenarios, it is noteworthy that the user of the medical device differs from the healthcare provider (i.e., the user of the configuration application). Information for the medical devices registered with a given configuration application may be stored by the configuration application and/or the update interface residing at the distribution server.

Product updates can then be distributed by the configuration device 30 at 34 to registered medical devices 18. Exemplary techniques for distributing the product updates are further described below. Upon successfully distributing a product update to a given medical device, a record of the product update is created and maintained in a transaction log by the configuration application. This record of the product update is communicated subsequently by the configuration application 30 at 35 to the update interface 24. To the extent that identifying information for the given medical resides at the configuration device, such identifying information is appended to the record communicated to the update interface 24. Upon receiving the update record, the update interface 24 will in turn update the audit database 28 regarding the product update.

Figure 6:
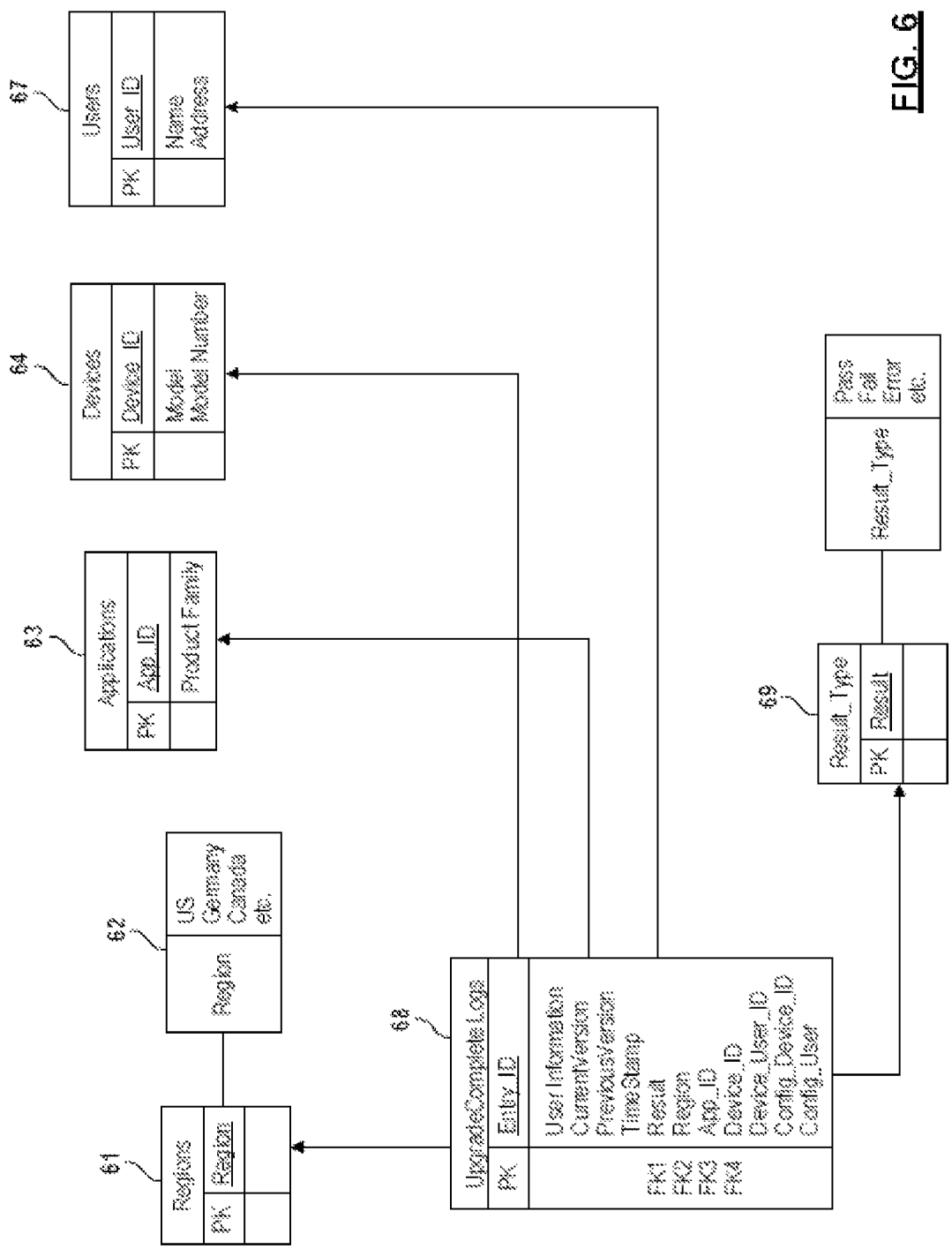
FIG. 6 is a diagram of an exemplary data model for the audit database.

FIG. 6 illustrates an exemplary data model for the audit log database 28. In an exemplary embodiment, the update interface 24 will create an upgrade complete log entry 68 for each product update. The primary key of the upgrade complete log entry 68 is a unique entry ID. Each entry will include information regarding the product update such as an identifier for the application update, a timestamp of when the update occurred as well as an indication of the update result. Each entry will also include identifying information for the configuration device (Config_Device_ID) and a user associated with the configuration application (Config_User) as well as identifying information for the given medical device (Device_ID). In some embodiments, the record may further include identifying information for the user associated with the given medical device (Device_User_ID). Thus, an entry has been created in the audit database 28 for each update to a given medical device. In the event of a product defect, the audit database 28 may be queried to determine which devices, if any, have been affected. Furthermore, the audit database 28 enables the update distributor (e.g., a device manufacturer) to contact the users of the medical devices either directly or via the healthcare provider who distributed the updates. Other implementations for the audit log database are contemplated by this disclosure.

Figure 7:
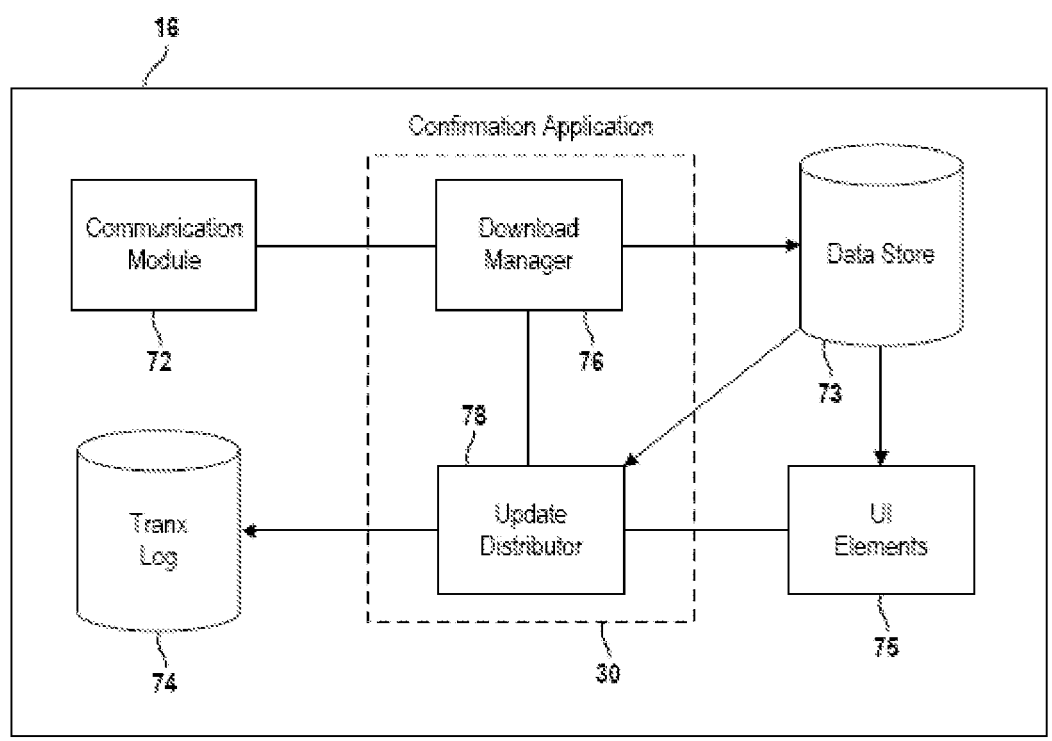
FIG. 7 is a diagram depicting an exemplary construct for the configuration device.

FIG. 7 illustrates an exemplary construct for the configuration device 16. In the exemplary embodiment, the configuration device 16 includes a configuration application 30, a communication module 72, a distribution data store 73, a transaction log 74 and one or more user interface components 75. More specifically, the configuration application 30 is comprised of a download manager 76 and an update distributor 78. The download manager 76 interfaces with the update interface 24 to download product updates in the manner set forth above. To do so, the download manager 76 is in data communication via the communication module 72 over a telecommunication network with the update interface 24 residing on the distribution server 14. For example, the download manager 76 may be connected by a modem over a telephone network or a computer network (e.g., the Internet) to the distribution server 14. In another example, the download manager 76 may be connected wirelessly via a cellular transceiver to the distribution server 14. Other types of communication modules and data links are contemplated by this disclosure. The download manager 76 stores the product updates downloaded from the distribution server 14 in the distribution data store 73 residing on the configuration device 16. In an exemplary embodiment, the distribution data store 73 may employ a data structure similar to the data model for the distribution database 26. In this way, the configuration device can subsequently distribute the product updates from the data store 73 to one or more medical devices 18 while offline from the distribution server 14.

The update distributor 78 is primarily responsible for distributing product updates to one or more medical devices 18. During operation, the update distributor 78 is configured to capture identifying information for the user who intends to distribute product updates to end user devices. For example, the update distributor 78 may learn the identity of the user during a sign-in procedure. In the case of a multi-practitioner healthcare provider, the user may be one of a plurality of users authorized to use the configuration application 30. In most situations, the user of the update distributor 78 differs from the user associated with the medical devices 18 receiving a product update from the update distributor 78.

Following a product update to a device, the update distributor 78 further operates to create a record for the product update in the transaction log 74. Since product updates can occur when the configuration device 16 is offline (i.e., not in data communication) from the distribution server 14, the configuration application 30 mandates updating the transaction log 74 for each product update. By enforcing maintenance of a transaction log 74, the configuration application 30 is able to provide a record for each product update back to the distribution server 14 for audit purposes. Upon initiating data communication with the distribution server 14 or periodically thereafter, the download manager 76 will upload the transaction log 74 to the update interface 24 which in turn updates the audit database 28 accordingly.

Figure 8:
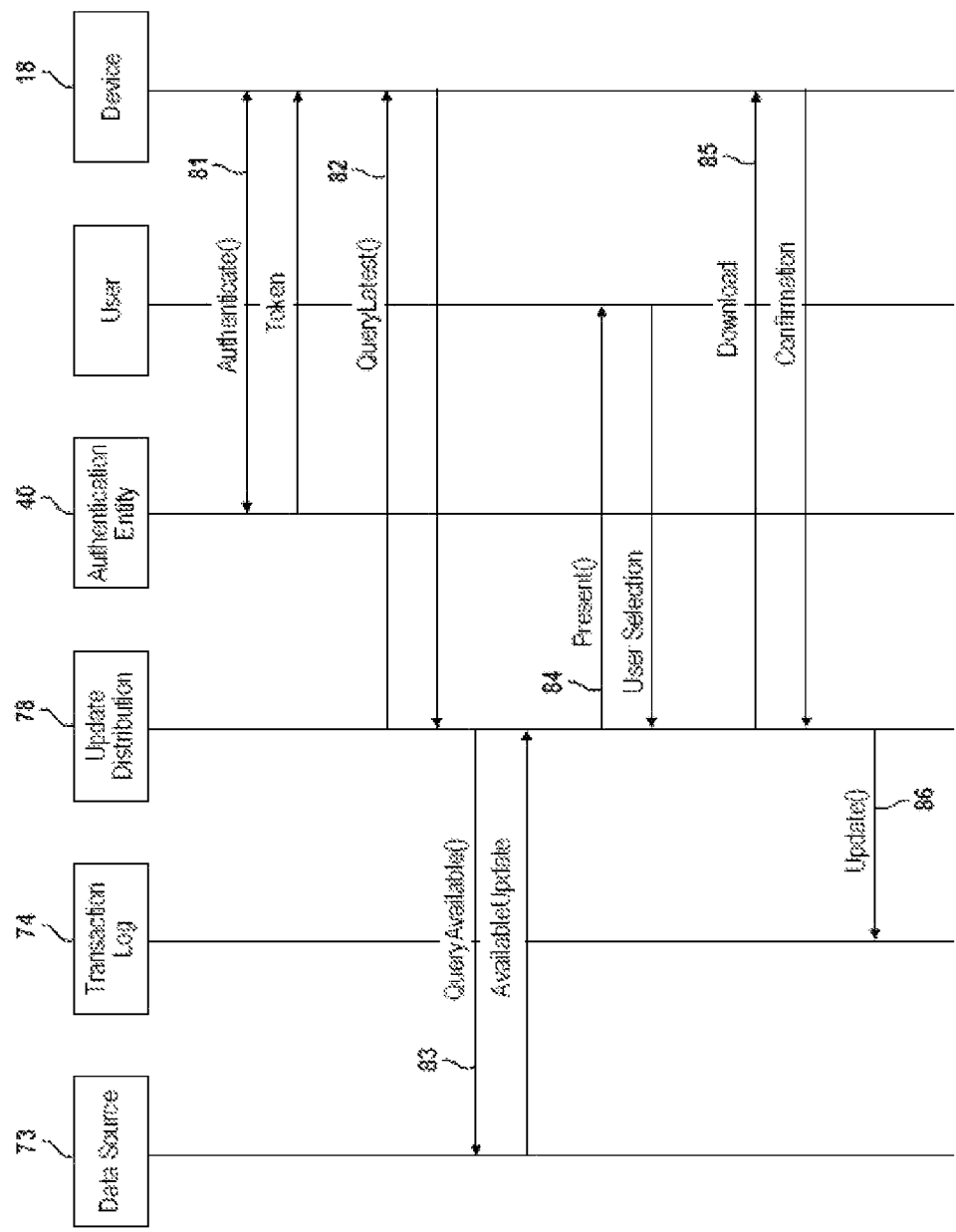
FIG. 8 is a diagram depicting an exemplary method for distributing product updates from the configuration device to one or more end user devices.

FIG. 8 illustrates an exemplary method for distributing product updates from the configuration device 16 to one or more medical devices 18. Before product updates can be distributed, a data link must be established between the configuration device 16 and a target user device 18. For example, communication between devices may be established using a USB connection or some other suitable communication data link. Once connected, the update distributor 86 may initiate the update process automatically or upon receipt of a command from a user.

In the exemplary embodiment, the update distributor 78 may first authenticate the target user device 18 as indicated at 81. Before it can receive product updates, a medical device 18 will register itself with the configuration application 30 as noted above. During the registration process, the configuration application 30 will capture information that uniquely identifies the medical device (e.g., device serial number). During authentication, this identifying information can be used authenticate the medical device 18. The authentication entity may reside on the configuration device or a separate distinct server. When successfully authenticated, the authentication entity 40 returns an authentication token to the medical device 18. Various authentication schemes are readily known and are suitable for use in this context. The medical device 18 may then use the authentication token while interfacing with the update distributor 78.

Next, the update distributor 78 will query the medical device at 82 to determine what packages and versions thereof reside on the medical device. The medical device is configured to provide a listing of such packages to the update distributor 78 in response to the query.

The update distributor 78 will also query distribution data store 73 at 83 to determine what product updates are available for a given medical device. The query may include information that further identifies the given medical device such as a device type or device serial number. This information may be used to constrain the query results. For example, a medical device having the type of blood glucose meter will result in a listing of product updates that vary from those of a medical device having a type of insulin pump. In response to the query, a listing of suitable product updates available for the given device is returned to the update distributor 78. The update distributor 78 may further narrow the listing of suitable product updates by comparing the version of an available package with the version of the package currently installed on the given medical device. Only those packages having a more current version would be included in the list of suitable product updates.

The listing of suitable product updates may be presented at 84 via a display or some other user interface component 75 of the configuration device 16 to the user of the configuration application 30. Given a listing of suitable product updates, the user can then select which product update, if any, to download to the end user device 18. Upon receipt of the user selections, the update distributor 78 initiates download of the product updates as indicated at 85. Alternatively, the update distributor 78 may forego presenting the listing of suitable product updates to the user and proceed to download each of the product updates suitable for the end user device without user intervention.

To complete the download, the medical device communicates a confirming message back to the update distributor 78. The confirming message may include a simple status indicator, such as pass or fail, or may provide a more comprehensive report regarding the installation of the product update on the medical device. Upon receipt of the confirming message, the update distributor 78 will update the transaction log as indicated at 88. The entry in the transaction log will include information of the product updates distributed as well as information identifying the medical device receiving the product updates.

Figure 9:
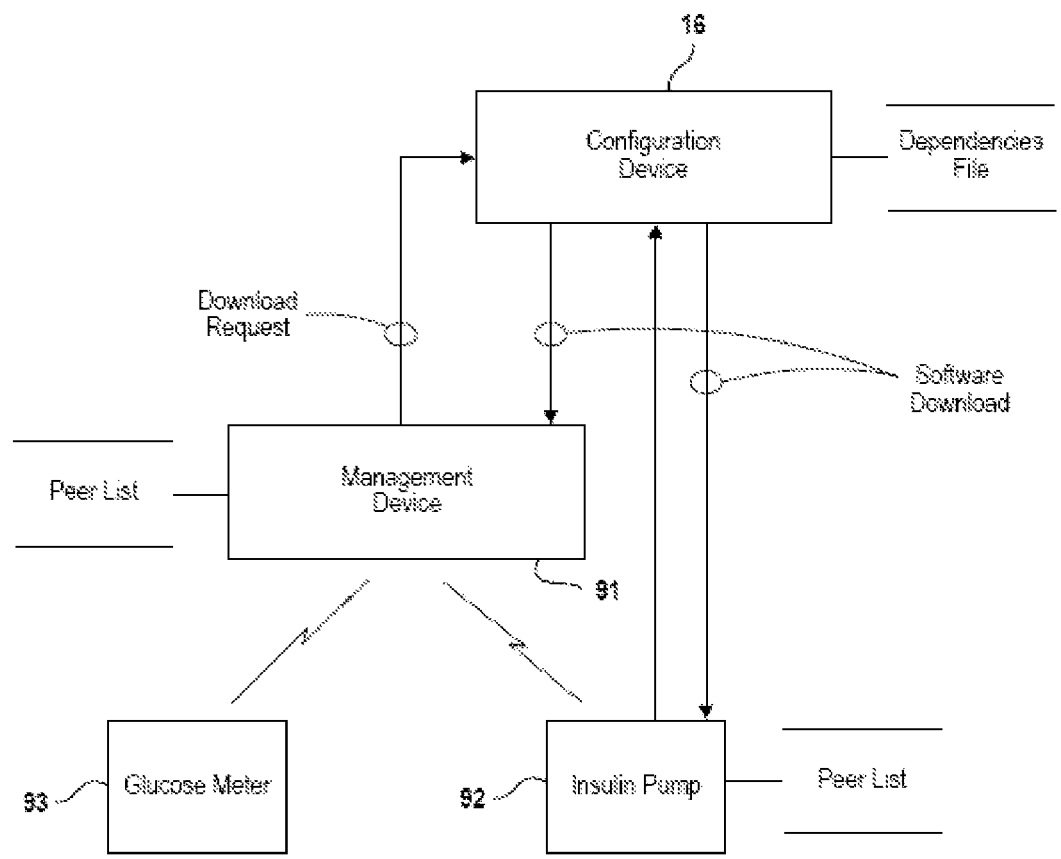
FIG. 9 is a diagram illustrating an exemplary use case for distributing product updates from a configuration device.

FIG. 9 illustrates an exemplary use case pertaining to medical devices used in diabetes care. In this example, a handheld diabetes management device 91 performs various tasks including measuring and recording blood glucose levels of a patient, determining an amount of insulin to be administered to the patient, scheduling tasks related to diabetes care, etc. In addition, the handheld diabetes management device 91 can transmit commands over a wireless data link to an insulin pump 92 which may in turn selectively deliver insulin to the patient in accordance with the commands. The handheld diabetes management device 91 may also receive and process blood glucose measures from a continuous glucose monitor 93 that senses blood glucose levels at periodic time intervals using a subcutaneous sensor. In these ways, the diabetes management device 91 is interoperable with the insulin pump 92 and the continuous glucose monitor 93.

Given this interoperability, there may be dependencies between software programs on these different devices. For example, the firmware on the continuous glucose meter 93 may not properly interface with an older version of a diabetes management software application residing on the diabetes management device 91. Similarly, the command set used by the diabetes management software application to interface with the insulin pump 92 may not be compatible with a more current version of software operating on the insulin pump 92. Accordingly, the digital distribution platform 10 should be configured to support distribution of product updates to a requesting device taking into account dependencies with other devices which are interoperable with the requesting device.

Figure 10:
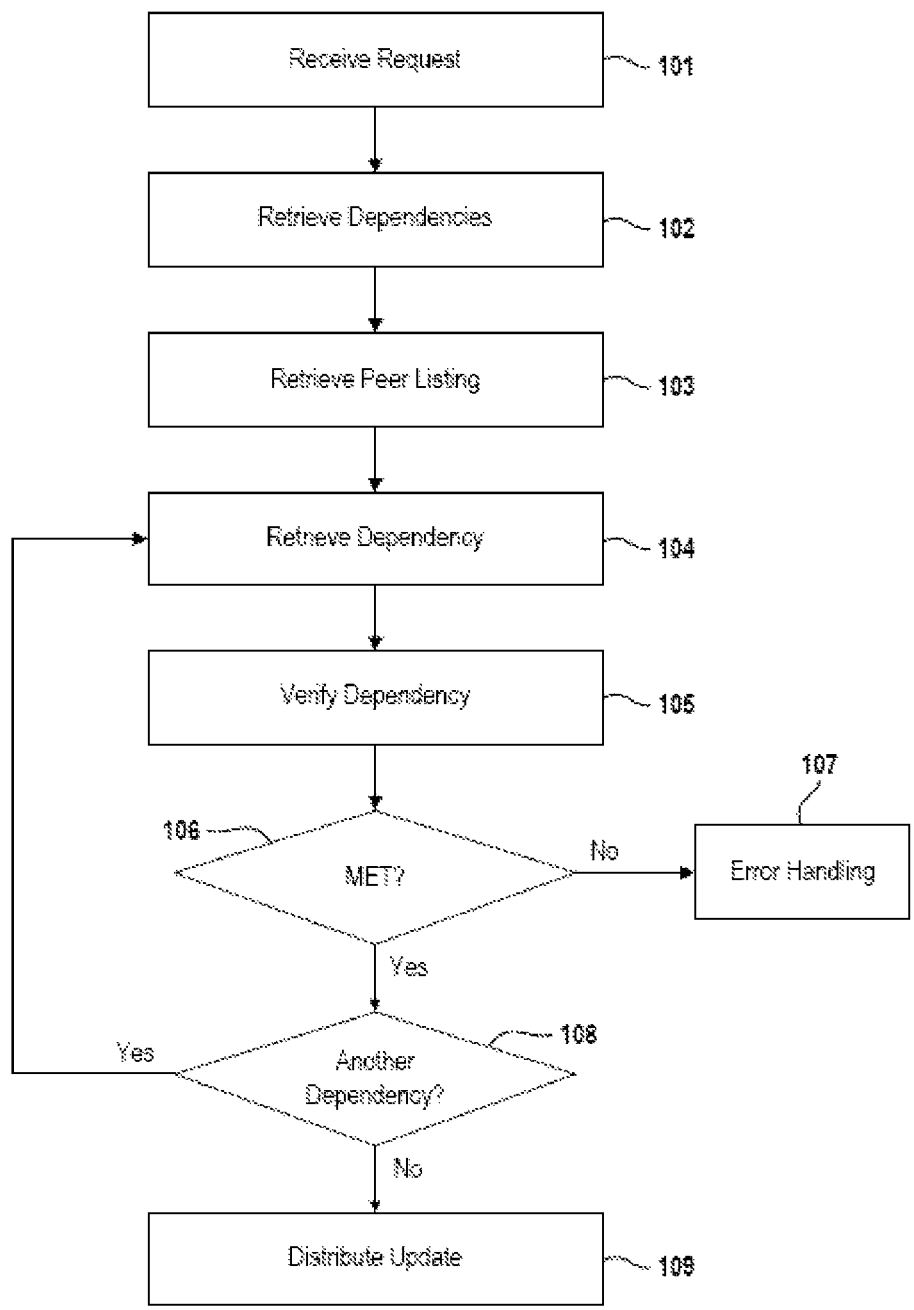
FIG. 10 is a flowchart depicting an exemplary method for distributing product updates which accounts for dependencies amongst devices.

FIG. 10 illustrates an exemplary method for distributing product updates from a configuration device 16 in the digital distribution platform 10. The configuration device 16 may interface with the distribution server 14 as well as one or more medical devices 18 in the manner described above. Although the distribution method is described as being carried out by the configuration device 16, it is readily understood that this method may also be implemented on the distribution server 14 when distributing product updates directly to the medical devices 18.

Upon receiving a request to download a product update at 101 from a requesting medical device, the configuration device 16 would first determine at 102 one or more dependencies that must be met before the product update can be downloaded to the requesting medical device. Dependencies for a product update are defined by the publisher of the product update and stored in the distribution database 26 along with other information regarding the product update. When a product update is downloaded from the distribution server 14 to the configuration device 16, dependency data for each product update is likewise downloaded to and stored on the configuration device 16.

Dependency data may be stored on the configuration device 16 in the distribution data store 73 which has a data structure similar to the distribution database 26. Alternatively, the dependency data may be stored in a separate data file residing on the configuration device 16. An exemplary layout for this data file is set forth below.

```
<package>
    <product> Homer diabetes manager</product>
    <type>Software</type>
    <value>4.0</value>
    <id>12345</id>
    <Dependencies>
        <dependency>
            <product>Odysseus pump manager</product>
            <type>Firmware</type>
            <value>2.0</value>
            <type>App-to-App</type>
            <key>13580</key>
        <dependency>
        <dependency>
            <product>Penelope continuous meter</product>
            <type>Software</type>
            <value>1.2</value>
            <type>App-to-App</type>
            <key>24690</key>
        <dependency>
        <dependency>
            <type>Region</type>
            <key>US</key>
        <dependency>
    </Dependencies>
</package>
```

In this example, the product update package is for a product called the 'Homer diabetes manager' which has a product type designated as 'software'. The unique identifier for this package is '12345' and the package pertains to version 4.0 of the product. Three dependencies have been defined for this package. First, this product update package requires that a certain version of the Odysseus pump manager firmware be installed on the insulin pump. Second, this product update package requires that a certain version of the Penelope operational software be installed on the continuous glucose meter. Note that each of these dependencies define an identifier <key> of the corresponding update package that package '12345' depends on. Such identifier can be used to retrieve additional information about the dependency from the dependency file. Third, this product update package is suitable for use in a particular geographic region and thus can only be installed on a requesting device being used in the particular geographic region. Either of the two storage means referenced above are referred to herein generally as the dependency file.

Before distributing a product update, the configuration device 16 must learn which devices are interoperable with the requesting medical device. In one exemplary embodiment, each device requesting a product update maintains a listing of peer devices (i.e., devices it is interoperable with). Peer devices may be added to the listing whenever a requesting medical device pairs with or otherwise establishes a communication link with another device. In another exemplary embodiment, the listing of peer devices may be downloaded from the distribution server 14 to the configuration device 16. For each peer device in the listing, the listing further includes an enumeration of software as well as associated data files residing on a given peer device. Continuing with the example set forth above, an exemplary layout for the listing of peer devices is as follows:

```
<Device_ID>
<Model Number>
<Device type>Insulin pump</device type>
<Products>
    <product>Odysseus pump manager</product>
    <type>Firmware</type>
    <value>2.0</value>
    <product>Ulysses user interface</product>
    <type>Software</type>
    <value>4.0</value>
<Device_ID>
<Model Number>
<Device type>Continuous glucose meter</device type>
    <product>Penelope continuous meter</product>
    <type>Software</type>
    <value>1.2</value>
```

In this way, dependencies between devices may be verified before a product update is distributed to a requesting medical device.

For a requested product update, dependencies are verified by the update distributor 78 of the configuration device 16. To do so, a dependency is retrieved at 104 from the dependency file. The dependency is then verified at 105. Verification of a dependency depends upon the dependency type. For example, a dependency for software specifies a version of that software that must reside on the peer device. In a simplified embodiment, each software entity in the listing of peer devices is checked against the retrieved dependency. When the product identifier for the software entity in the listing matches the product identifier for the dependency, the version of the software in the listing is compared to the specified version of the software in the dependency. The dependency is met or satisfied when the software residing on the peer device has a version as recent as the version of software specified by the dependency. In a typical versioning scheme, versions are ordered in ascending order such that any version higher than the specified version would satisfy the dependency.

In a more robust embodiment, dependencies may specify the type of device the software resides on. When the software specified by a dependency is not found in the listing of peer device for a device having a matching device type, the dependency is not met.

A dependency having a region type specifies the intended geographic area of use for the product update. To verify this dependency, the update distributor receives an identifier for the geographic region associated with the requesting medical device. In one embodiment, the identifier accompanies the request to download a product update from the requesting device. When the value for the region type matches the identifier for the geographic region, the dependency is met.

When a given dependency has been satisfied, another dependency is retrieved and verified as indicated at 108 until all of the dependencies associated with the product update have been verified. If a given dependency is not met, then the update distributor will proceed with error processing as indicate at 107. In one embodiment, the product update is aborted and the user is notified of the compatibility issue. In this exemplary embodiment, when each of the dependencies for the product update has been met, the product update is distributed at 109 to the requesting device. In other embodiments, two or more dependencies may be defined as OR conditions. It is readily understood that the verification procedure could be modified to accommodate such conditions between dependencies.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same can also be varied in many ways. Such variations are not to be regarded as a departure from the disclosure, and all such modifications are intended to be included within the scope of the disclosure.

What is claimed is:

1. A computer-implemented method for distributing product updates from a configuration device to one or more handheld medical device(s), comprising
receiving, by the configuration device, a request to download a product update to a requesting medical device,
retrieving, by the configuration device, a dependency that must be met before the product update can be downloaded to the requesting medical device, where the at least one dependency specifies a version of software that resides on a device which is interoperable with the requesting medical device,
receiving, by the configuration device, a listing of peer devices from the requesting medical device, such that each peer device in the listing of peer devices is distinct from and interoperable with the requesting medical device and each peer device includes an enumeration of software residing thereon including a version for the software,
for each peer device in the listing of peer devices, determining, by the configuration device, software residing on a given peer device from the listing of peer devices,
comparing, by the configuration device, the version of software specified by the dependency to the version of the corresponding software in the listing of peer devices, and
distributing, by the configuration device, the product update to the requesting medical device when the software residing on each peer device in the listing of peer devices is compatible with the version of software specified by the dependency,
determining a first dependency that specifies a version of a first software entity and a second dependency that specifies a version of a second software entity, and distributing the product update to the requesting medical device when the first and second dependencies are met, where the first and second software entities reside on different peer devices.

2. The method of claim 1 further comprises downloading software available for distribution over a telecommunication network from a distribution server to the configuration device and storing the available software in a data store residing on the configuration device.

3. The method of claim 2 further comprises downloading a dependency file from the distribution server to the configuration device and determining one or more dependencies that must be met before the product update can be downloaded from the dependency file.

4. The method of claim 1 further comprises maintaining a listing of peer devices at the given medical device and communicating the listing of peer devices from the given medical device to configuration device, where the listing include an enumeration of software residing on each peer device in the listing.

5. The method of claim 1 further comprises distributing the product update to the requesting medical device when the software residing on the each peer device has a version as recent as the version of software specified by at least one dependency.

6. The method of claim 1 further comprises receiving an identifier for the geographic region associated with the requesting medical device; comparing the identifier to another dependency; and distributing the product update to the requesting medical device when the another dependency is met, where the another dependency specifies an intended geographic area of use for the product update.

7. The method of claim 1 further comprises determining one or more dependencies that specify a version of software that resides on the requesting medical device and distributing the product update to the requesting medical device when each of the one or more dependencies are met.

8. The method of claim 1 further comprises defining at least one of the first and second software entities as a data file.

9. A software configuration device for distributing product updates to one or more handheld medical devices, comprising:
a distribution data store residing in a non-transitory memory and operable to store one or more product updates available for distribution;
a dependency file residing in a non-transitory memory and operable to store one or more dependencies for a given product update that must be met before the product update can be downloaded; and an update distributor configured to receive a request to download the given product update from a requesting medical device and, in response to the download request, retrieve the one or more dependencies for the given product update from the dependency file, where at least one of the dependencies for the given product update specifies a version of software that resides on a device which is interoperable with the requesting medical device;

the update distributor further configured to receive a listing of peer devices that are interoperable with the requesting medical device and, in response to the download request, compares the at least one dependency with software residing on each peer device in the listing of peer devices and distributes the given product update to the requesting medical device when the at least one dependency is met, where the update distributor is implemented as computer executable instructions executed by a computer processor of the software configuration device, wherein the update distributor is operable to determine a first dependency that specifies a version of a first software entity and a second dependency that specifies a version of a second software entity, and distribute the given product update to the requesting medical device when the first and second dependencies are met, where the first and second software entities reside on different peer devices.

10. The configuration device of claim 9 further comprises a download manager in data communication over a telecommunication network with a distribution server, the download manager configured to retrieve software available for distribution from the distribution server and store the available software in the distribution data store residing on the configuration device.

11. The configuration device of claim 10 wherein the download manager further retrieves the dependency file from the distribution server.

12. The configuration device of claim 9 wherein the update distributor is configured to receive the listing of peer devices from the requesting medical device, the listing includes an enumeration of software residing on each peer device in the listing.

13. The configuration device of claim 9 wherein the update distributor operates to distribute the given product update to the requesting medical device when the software residing on the each peer device has a version as recent as the version of software specified by the at least one dependency.

14. The configuration device of claim 9 wherein the update distributor is configured to receive an identifier for the geographic region associated with the requesting medical device from the requesting medical device, the update distributor operable to compare the identifier to another dependency and distribute the given product update to the requesting medical device when the another dependency is met, such that the another dependency specifies an intended geographic area of use for the product update.

15. The configuration device of claim 9 wherein the update distributor is operable to determine one or more dependencies that specify a version of software that resides on the requesting medical device and distribute the given product update to the requesting medical device when each of the one or more dependencies are met.

16. A computer-implemented method for distributing product updates from a configuration device to one or more handheld medical devices, comprising
- receiving, by the configuration device, a request to download a product update to a requesting medical device,
- receiving, by the configuration device, a listing of peer devices from the requesting medical device, such that each peer device in the listing of peer devices is distinct from and interoperable with the requesting medical device and each peer device includes an enumeration of software residing thereon including a version for the software;
- for each peer device in the listing of peer devices, determining, by the configuration device, software residing on a given peer device from the listing of peer devices;
- retrieving, by the configuration device, a first dependency that must be met before the product update can be downloaded to the requesting medical device, where the first dependency specifies a version of a first software entity that resides on a device which is interoperable with the requesting medical device;
- retrieving, by the configuration device, a second dependency that must be met before the product update can be downloaded to the requesting medical device, where the second dependency specifies a version of a second software entity that resides on a device which is interoperable with the requesting medical device;
- comparing, by the configuration device, the version of software specified by the first and second dependencies to the version of corresponding software in the listing of peer devices; and
- distributing the product update to the requesting medical device when the first and second dependencies are met, where the first and second software entities reside on different peer devices.

* * * * *